United States Patent [19]
Getman et al.

[11] Patent Number: 5,273,981
[45] Date of Patent: Dec. 28, 1993

[54] INTRAMOLECULAR CARBAMATE DERIVATIVE OF 2,3-DI-O-BLOCKED-1,4-DIDEOXY-4-FLUORO-NOJIRIMYCINS

[75] Inventors: Daniel P. Getman, St. Louis; Gary A. DeCrescenzo, St. Peters, both of Mo.

[73] Assignee: Monsanto Company, St. Louis, Mo.

[21] Appl. No.: 868,937

[22] Filed: Apr. 16, 1992

Related U.S. Application Data

[62] Division of Ser. No. 599,596, Oct. 18, 1990, Pat. No. 5,128,347.

[51] Int. Cl.$^5$ .............. A61K 31/435; C07D 498/04
[52] U.S. Cl. ...................... 514/302; 546/116
[58] Field of Search ................. 546/116; 514/302

[56] References Cited

U.S. PATENT DOCUMENTS

| | | | |
|---|---|---|---|
| 4,260,622 | 4/1981 | Junge et al. | 546/200 |
| 4,639,436 | 1/1987 | Junge et al. | 546/200 |
| 5,003,072 | 3/1991 | Partis et al. | 546/243 |
| 5,025,021 | 6/1991 | Getman et al. | 514/302 |
| 5,026,713 | 6/1991 | Getman et al. | 514/302 |
| 5,028,614 | 7/1991 | Liu et al. | 514/306 |
| 5,030,638 | 7/1991 | Partis et al. | 514/315 |
| 5,034,517 | 7/1991 | Umezawa et al. | 536/18.5 |
| 5,041,555 | 8/1991 | Fleet et al. | 548/541 |

OTHER PUBLICATIONS

Heiker et al., Carbohydrate Res., 203(2), pp. 314–318 (Aug. 15, 1990).
Wuensche et al., Org. Mass Spectrometry, 19(4), pp. 176–182 (1984).
Heiker, F. R. et al., "Synthesis of D-galacto-1-deoxynojirimycin (1,5-dideoxy-1,5-iminoD-galactitol) Starting From 1-Deoxynojirimycin", *Carbohydrate Research*, 203, pp. 314–318 (1990).
Schueller, A. M. et al., "Synthesis of 2-Acetamido-1,-2-ideoxy-D-galactonojirimycin(1-acetamido)-1,2,5-trideoxy-1,5-imino-D-galactitol) From 1-Deoxynojiimycin", *Carbohydrate Research*, 203, pp. 308–313 (1990).
Withers, S. G. et al., "2-Deoxy-2-fluoroglucosides: A Novel Class of Mechanism-Based Glucosidase Inhibitors", *J. Am. Chem. Soc.*, 109, pp. 7530–7531 (1987).
Bernotas, R. C. et al., "Synthesis of (+)-1,5-dideoxy-1,5-imino-D-galactitol, a potent α-D-galactosidase inhibitor", *Carbohydrate Research*, 167, pp. 305–311 (1987).
Wünsche, C. et al., "Comparison of 'Soft Ionization' Techniques with Electron Impact Mass Spectrometry for Desoxinojirimycin and Folic Acid Derivatives", *Organic Mass Spectrometry*, vol. 19, No. 4, pp. 178–182 (1984).

*Primary Examiner*—Bernard Dentz
*Attorney, Agent, or Firm*—Kenneth D. Goetz

[57] ABSTRACT

Novel compounds represented by the formula:

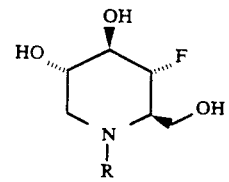

wherein R represents hydrogen, alkyl radicals having from 1 to about 10 carbon atoms, alkenyl radicals having from 1 to about 10 carbon atoms, aryl, alkaryl and aralkyl radicals having from about 6 to about 16 carbon atoms and acyl and acyloxy radicals having from about 1 to about 10 carbon atoms, manifest glycosidase inhibition activity.

7 Claims, No Drawings

INTRAMOLECULAR CARBAMATE DERIVATIVE OF 2,3-DI-O-BLOCKED-1,4-DIDEOXY-4-FLUORO-NOJIRIMYCINS

This is a division of application Ser. No. 07/599,596, filed Oct. 18, 1990 now U.S. Pat. No. 5,128,347.

BACKGROUND OF THE INVENTION

1. Field of the Invention

This invention relates to novel piperidine derivatives which manifest glycosidase inhibition activity and to novel intermediates useful in the manufacture thereof. The present invention also relates to methods for preparing such derivatives and intermediates.

More particularly, the present invention relates to 3-fluoro analogs of 2-hydroxymethyl-4, 5,-dihydroxypiperidines, which are the ring nitrogen analogs of 1-deoxy-D-glucose and are generally referred to as 1-deoxynojirimycin (DNJ) analogs. More particularly, the present invention relates to 1,4-dideoxy-4-fluoronojirimycin and the corresponding N-derivatives; to intermediates useful in preparing such fluorinated analogs; to methods for preparing the intermediates beginning with 1-deoxynojirimycin as starting material; and to methods for preparing the 4-fluoro analogs utilizing such intermediates.

2. Related Art

1-Deoxynojirimycin is a known glucosidase inhibitor. See, for example, Truscheit et al., Ang. Chemie Int'l. Ed., 20, 744 (1981). Fluoro analogs of glucose and glucose derivatives are also known. For example, see Withers et al, J.Amer. Chem. Soc., 109, 7530-31 (1987), and "Fluorinated Carbohydrates: Chemical and Biochemical Aspects; ACS Symposium Series 184," ed. N.F. Taylor, American Chemical Society (1988).

Böshagen, U.S. Pat. No. 4,940,705 discloses certain N-amide derivatives of 1-deoxynojirimycin and 1-deoxymannojirimycin.

SUMMARY OF THE INVENTION

The present invention is directed at 1,4-dideoxy-4-fluoronojirimycin and the N-derivatives thereof. These compounds are prepared utilizing novel 2,3-di-O-benzyl-1,4-dideoxy-4-fluoronojirimycin; N,6-O-carbamoyl-2,3-di-O-benzyl-1,4-dideoxy-4-fluoronojirimycin; N,6-O-carbamoyl-2,3-di-O-benzyl-1,5-dideoxy-4-ketonojirimycin; N,6-O-carbamoyl-2,3-di-O-benzyl-1,5-dideoxy-1,5-imino-D-galactitol; and N,6-O-carbamoyl-2,3-di-O-benzyl-1-deoxynojirimycin intermediates which are then utilized to produce the subject compounds.

DETAILED DESCRIPTION OF THE INVENTION

The present invention resides in the discovery that novel 4-deoxy-4-fluoro analogs of 1-deoxynojirimycin and the N-derivatives thereof manifest glycosidase inhibition activity. The subject compounds can be represented by the formula:

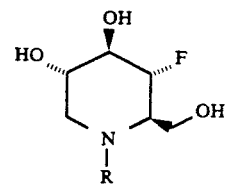

wherein R represents hydrogen, alkyl radicals having from 1 to about 10 carbon atoms, alkenyl radicals having from 1 to about 10 carbon atoms, aryl, alkaryl and aralkyl radicals having from about 6 to about 16 carbon atoms, and acyl and acyloxy radicals having from about 1 to about 10 carbon atoms. Accordingly, the present invention is directed to such novel analogs, to novel intermediates useful in the manufacture of such analogs, and to methods for preparing such novel intermediates and analogs.

These novel analogs and intermediates can be represented generically by the formula:

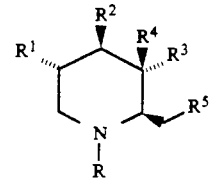

wherein R represents hydrogen, alkyl radicals having from 1 to about 10 carbon atoms, alkenyl radicals having from 1 to about 10 carbon atoms, aryl, alkaryl and aralkyl radicals having from about 6 to about 16 carbon atoms and acyl and acyloxy radicals having from about 1 to about 10 carbon atoms; $R^1$ and $R^2$ independently represent hydroxy, benzyl and allyl ethers, and acyl esters represented by the following formula:

$$R^6{-}\overset{O}{\underset{\|}{C}}{-}O$$

wherein $R^6$ represents alkyl radicals having from 1 to about 10 carbon atoms and aryl, aralkyl and alkaryl radicals; $R^3$ represents, fluorine, hydrogen and hydroxy; $R^4$ represents hydrogen and hydroxy; or $R^3$ and $R^4$ together represent keto; $R^5$ represents hydroxy or together with R represents a cyclic carbamate to form a compound of the formula:

provided that when $R^3$ is fluorine, $R^4$ is hydrogen, and when $R^4$ is hydroxy, $R^3$ is hydrogen.

More particularly, the novel analogs can be represented by the formula:

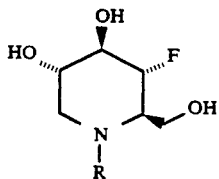

wherein R represents hydrogen, alkyl radicals having from 1 to about 10 carbon atoms, alkenyl radicals having from 1 to about 10 carbon atoms, aryl, alkaryl and aralkyl radicals having from about 6 to about 16 carbon atoms and acyl and acyloxy radicals having from about 1 to about 10 carbon atoms.

The 2,3-di-O-benzyl-1,4-dideoxy-4-fluoronojirimycin intermediate can be represented by the formula:

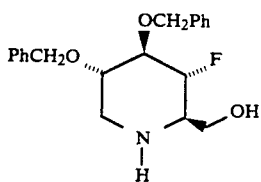

The N,6-O-carbamoyl-2,3-di-O-benzyl-1,4-dideoxy-4-fluoronojirimycin intermediate can be represented by the formula:

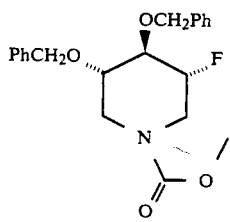

The N,6-O-carbamoyl-2,3-di-O-benzyl-1,5-dideoxy-1,5-imino-D-galactitol can be represented by the formula:

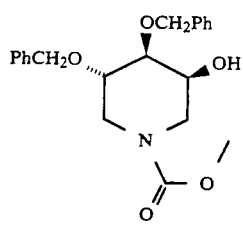

The N,6-O-carbamoyl-2,3-di-O-benzylbenzyl-1,5-dideoxy-4-ketonojirimycin can be represented by the formula:

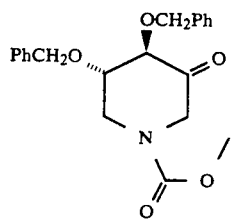

The N,6-O-carbamoyl-2,3-di-O-benzyl-1-deoxynojirimycin can be represented by the formula:

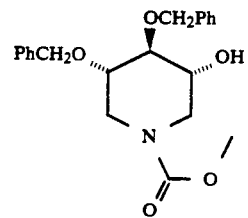

The 1,4-dideoxy-4-fluoronojirimycin compound of the present invention can be prepared beginning with 1-deoxynojirimycin (hereinafter referred to as "DNJ"), which can be prepared by known procedures as disclosed in U.S. Pat. Nos. 4,220,782; 4,246,345; and 4,806,650. The corresponding N-alkyl derivatives can then be prepared according to known procedures. See, for example, U.S. Pat. Nos. 4,220,782; 4,266,025; 4,405,714; 4,806,650; and 4,940,705.

The compounds of the present invention are prepared starting with DNJ, protecting the amino group, preferably with a carbobenzoxy group, and then protecting the 4-hydroxy and 6-hydroxy groups, preferably utilizing the benzylidene protecting group. Introduction of the carbobenzoxy group is generally conducted in a polar solvent and in the presence of a base at a temperature of from about 0° C. to about 50° C., preferably from about 0° C. to about 25° C. such as from about 10° C. to 20° C. Exemplary bases include $NaHCO_3$, NaOH and certain tertiary amines. Exemplary solvents include water and N,N-dimethylformamide. The 4-hydroxy and 6-hydroxy groups are then protected by techniques well known to those familiar with carbohydrate chemistry. These N-protected-4,6-O-protected derivatives can be represented by the formula:

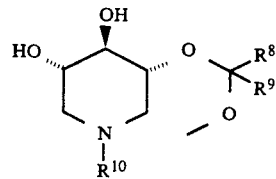

wherein $R^8$ and $R^9$ independently represent hydrogen, alkyl radicals having from 1 to about 10 carbon atoms, and aryl radicals; and $R^{10}$ represents a carbonyl compound as described below. For example, utilizing 2,2-dimethoxypropane or, preferably, benzaldehyde, the corresponding 4,6-0-isopropylidene ($R^8=R^9=CH_3$) or 4,6-O-benzylidene ($R^8$=phenyl, $R^9$=H) N-substituted DNJ can be produced. These reactions are generally conducted in an inert organic solvent and in the presence of a strong acid which acts as catalyst. The reactions can be conducted at temperatures of from about 0° C. to about 50° C., preferably from about 10° C. to 40° C., such as from about 20° C. to about 30° C. Exemplary acid catalysts include zinc chloride, p-toluenesulfonic acid and the like. During the reaction water is removed, preferably utilizing a molecular sieve such as a 3 angstrom (Å) molecular sieve. The amino protecting group can then be removed by procedures well known in the art, such as with a base, e.g., KOH, NAOH, and LiOH in a later step as discussed below.

The hydroxy groups at the 2 and 3 positions of the above-described N-protected-4,6-O-protected-1-deoxynojirimycin are then protected utilizing procedures which are well known in the art. For example, the N-protected-4,6-O-protected-1-deoxynojirimycin can be reacted with benzyl bromide, sodium hydride and tetra-n-butylammonium iodide in refluxing THF in order to dibenzylate such compound. Following dibenzylation, the next step involves removal of the 4,6-O-protecting group, e.g., the benzylidene group, by methods well known to those skilled in the art. Generally, such protecting groups can be removed utilizing an acid in an appropriate solvent at room temperatures. For example, $CF_3CO_2H$ in water, $CH_3CO_2H$ in water or HCl in water can be utilized to effectively deprotect the 4- and 6-hydroxy groups.

The resulting N-carbobenzoxy-2,3-di-O-benzyl-1-deoxynojirimycin is then reacted with a stoichiometric amount of suitable base to cyclize the C-6 hydroxy to afford the cyclic carbamate. Suitable bases include dialkyltin oxides, $NaHCO_3$, NaOH, pyridine, N,N-dimethyl-4-aminopyridine, DBU and the like. For example, di-n-butyltin oxide can be utilized in refluxing toluene with azeotropic removal of water to cyclize the C-6 hydroxy with displacement of benzyl alcohol to afford the cyclic carbamate represented by the formula:

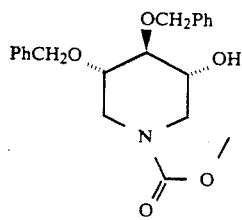

The C-4 hydroxyl group of the N,6-O-carbamoyl-2,3-di-O-benzyl-1-deoxynojirimycin is then inverted by oxidation to the ketone followed by reduction as described below. Oxidation to the ketone can be carried out utilizing well known procedures. For example, utilizing pyridinium chlorochromate, pyridinium dichromate, or Swern reagents (dimethylsulfoxide, trifluoroacetic anhydride or oxallyl chloride, and triethylamine) in an inert solvent, e.g., methylene chloride. The ketone intermediate can be represented by the formula:

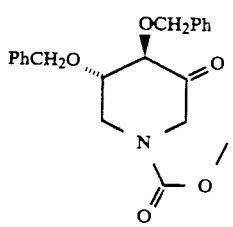

The ketone is then reduced with sodium borohydride in a suitable solvent system, e.g., THF, MEOH, and the like, icluding mixtures thereof. A preferred reaction is conducted in a mixture of THF and MEOH as the solvent system. The resulting product N,6-O-carbamoyl-2,3-di-O-benzyl-1,5-dideoxy-1,5-imino-D-galactitol can be represented by the formula:

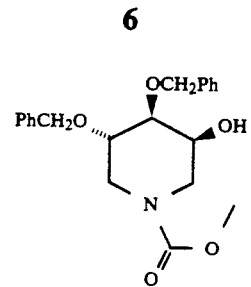

The N,6-O-carbamoyl-2,3-di-O-benzyl-1,5-dideoxy-1,5-imino-D-galactitol is then reacted with a fluorine source with inversion of configuration at C-4 to produce the corresponding N,6-O-carbamoyl-2,3-di-O-benzyl-1,4-dideoxy-4-fluoronojirimycin represented by the formula:

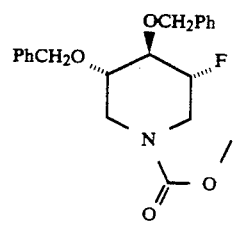

The reaction is preferably conducted in an inertsolvent, e.g., methylene chloride, benzene, toluene, chloroform, THF, and the like, at a temperature of between about $-80°$ C. and about $120°$ C., preferably between about $0°$ C. and about $85°$ C. Exemplary fluorine sources include those represented by the formula:

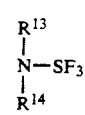

wherein $R^{13}$ and $R^{14}$ independently represent optionally substituted alkyl groups having from 1 to about 6 carbon atoms. A preferred alkyl group is ethyl.

Alternatively, the inverted alcohol can first be activated by conversion to its trifluoromethanesulfonate or p-methylbenzenesulfonate derivative and then displaced by a fluoride source in a suitable solvent. Suitable fluoride sources include cesium fluoride, potassium hydrogen fluoride, tetraalkylammonium fluorides, e.g., tetra-n-butylammonium fluoride, and tris(dimethylamino)sulfur (trimethylsilyl)difluoride. Suitable solvents include acetonitrile and N,N-dimethylformamide. This reaction is conducted at a temperature of between about $-80°$ C. and $120°$ C.

The N,6-O-carbamoyl-2,3-di-O-benzyl-1,4-dideoxy-4-fluoronojirimycin is then reacted with a suitable base, e.g., NAOH, to remove the N,6-O-carbamoyl moiety. This reaction is conducted under reflux in a suitable solvent such as, for example, THF, methanol and the like, including mixtures thereof. The resulting product is 2,3-di-O-benzyl-1,4-dideoxy-4-fluoronojirimycin.

The next step involves removal of the protecting group, e.g., the benzyl group, at the C-2 and C-3 hydroxy groups. The benzyl groups can be removed via hydrogenolysis utilizing palladium on carbon. Ester groups can be removed in a variety of ways well known to those skilled in the art. For example, the ester protecting groups can be removed utilizing lithium hydroxide, sodium hydroxide or potassium hydroxide in aqueous tetrahydrofuran. A preferred method for removal of ester groups utilizes sodium methoxide in methanol.

The subject 1,4-dideoxy-4-fluoronojirimycin and N-derivatives thereof manifest glycosidase inhibition activity. It is contemplated that certain intermediates disclosed herein will manifest similar activity. Thus, pharmaceutical compositions comprising one or more of the fluoro analogs and/or intermediates can be administered to a patient for this purpose. Such compositions, which may contain acceptable diluents and/or carriers, can be prepared by reference to general texts in the field such as, for example, Remington's Pharmaceutical Sciences, Ed. Arthur Osol, 16th ed., 1980, Mack Publishing Co.

Contemplated equivalents of the general formulas set forth above for the DNJ analogs and derivatives as well as the intermediates are compounds otherwise corresponding thereto and having the same general properties wherein one or more of the various R groups are simple variations of the substituents as defined therein, e.g., wherein R is a higher alkyl group. In addition, where a substituent is designated as, or can be, a hydrogen, the exact chemical nature of a substituent which is other than hydrogen at that position is not critical so long as it does not adversely affect the overall activity and/or synthesis procedure.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

EXAMPLE 1

Preparation of N-Carbobenzoxy-4,6-O-benzylidene-1-deoxynojirimycin

A total of 75.0 g (0.46 moles) of 1-deoxynojirimycin was dissolved in 1500 mL of saturated aqueous sodium bicarbonate and then treated with 73.5 mL (87.8 g, 0.52 moles) of 954 benzyl chloroformate at room temperature using an overhead stirrer under a nitrogen atmosphere for eighteen hours. The solution was extracted once with 250 mL of methylene chloride to remove any benzyl chloride and unreacted benzyl chloroformate. The aqueous solution was then extracted ten times with 500 mL of ethyl acetate. After drying over anhydrous magnesium sulfate, filtering and removal of solvent, 102.8 g (76% yield) of a colorless oil was obtained which was identified as N-carbobenzoxy-1-deoxynojirimycin of sufficient purity for use in the next step; 300 MHz $^1$H NMR ($\delta$, CD$_3$OD) 7.40–7.20 (m, 5H), 5.15 (s, 2H), 4.23 (br m, 1H), 4.05 (br d, J=8.0 Hz, 1H), 3.87 (dd, J=4.0 and 6.0 Hz, 1H), 3.85–3.d78 (m, 2H), 3.78–3.70 (m, 2H), and 3.45 (br d, J=8.0 Hz, 1H).

To 102 g (0.345 mol) of N-carbobenzoxy-1-deoxynojirimycin, which had been dried in vacuo over phosphorous pentoxide overnight, was added 1000 mL of benzaldehyde (dried with 3 Å molecular sieves). This was warmed at 40° C. while swirling on a rotary evaporator (no vacuum) until the oil was fully dissolved, then split in half and each half transferred to a 5 L three-necked flask and an additional 200 mL of benzaldehyde used to rinse the flask and 100 mL added to each reaction. After placing each reaction flask under nitrogen, 101 g of freshly activated 3 Å molecular sieves were added and then 257.6 g of anhydrous zinc chloride (dried in vacuo overnight over P$_2$O$_5$) was added and some warming observed. After stirring for five hours at room temperature, 1000 mL of ethyl acetate was added, each flask cooled in an ice bath and then 1500 ML of a cold saturated aqueous solution of sodium bicarbonate was added. Some foaming was observed. The white precipitate which formed was filtered and washed with ethyl acetate. The filtrate was separated and the organic layer washed with saturated sodium chloride, dried with magnesium sulfate and filtered. The organic layer from each reaction were combined and stripped at 40° C. to afford a benzaldehyde solution of the desired product. This was then poured into 10 L of hexane with stirring, the precipitate collected and washed with hexane and air dried. This material was dissolved in approximately 1200 mL of hot ethyl acetate, hexane added to the cloud point (approx. 1500 mL), where-upon crystallization occurred. After cooling to room temperature, the precipitate was collected and washed well with hexane to afford 91.1 g (68%) of N-carbobenzoxy-4,6-O-benzylidene-1-deoxynojirimycin as a white solid, mp 147°–148° C.; 300 MHz $^1$H NMR ($\delta$, CD$_3$OD) 7.53–7.28 (m, 10H), 5.61 (s, 1H), 5.14 (s, 2H), 4.77 (dd, J$_{5,6}$=4.6 Hz, J$_{6,6'}$=11.0 Hz, 1H, H$_6$) 4.38 (t, J$_{5,6'}$=J$_{6,6'}$=11.0 Hz, 1H, H$_{6'}$), 4.16 (dd, J$_{1,2}$=4.2 Hz, J$_{1,1'}$=13.4 Hz, 1H, H$_1$), 3.69–3.50 (complex m, 3H, H$_2$, H$_3$ and H$_4$), 3.35 (ddd, J$_{4,5}$=J$_{5,6'}$=11.0 Hz, J$_{5,6}$=4.6 Hz, 1H, H$_5$) and 2.97 (dd, J$_{1',2}$=9.3 Hz, J$_{1,1'}$=13.4 Hz, 1H, H$_{1'}$); 75 MHz $^{13}$C NMR (CD$_3$OD) 156.7, 139.4, 138.0, 129.9, 129.7, 129.3, 129.2, 129.1, 127.6, 102.8, 81.9, 77.5, 71.5, 70.6, 68.6, 55.9 and 50.5 ppm; mass spectrum (m/e) 386 (M+H), 361, 327 and 280; and Anal. Calcd. for C$_{21}$H$_{23}$NO$_6$: C (65.45), H (6.01) and N (3.63); Found C (65.41), H (6.19) and N (3.59).

EXAMPLE 2

Preparation of N-Carbobenzoxy-2,3-di-O-benzyl-4,6-O-benzylidene-1-deoxynojirimycin After washing 5.60 g (2.4 eq) of an 80% sodium hydride dispersion in oil with hexanes, 10 mL of anhydrous tetrahydrofuran was added under a nitrogen atmosphere. To this was then added dropwise 30 g (0.078 mol) of N-carbobenzoxy-4,6-O-benzylidene-1-deoxynojirimycin in 250 mL of anhydrous tetrahydrofuran. After gas evolution had ceased the reaction was charged with 32 g (22.2 mL, 2.4 eq) of benzyl bromide and 5.7 g (15 mole %) of tetra-n-butyl ammonium iodide and refluxed for 24 hours. The reaction mixture was filtered through a fritted glass funnel, and the filtrate was diluted with 200 mL of dichloromethane and washed with 200 mL of water, 200 mL of 1N hydrochloric acid, saturated aqueous sodium bicarbonate and dried over MgSO₄. The solution was concentrated in vacuo and purified by column chromatography using 10-20% ethyl acetate/hexane. The recovered diol (~10 g) was resubjected to the benzylation procedure and purified as before. The combined batches of dibenzyl product was recrystallized from dichloromethane/hexane to yield 27.2 g (63% yield) of the desired N-carbobenzoxy-2,3-di-O-benzyl-4,6-O-benzylidene-1-deoxynojirimycin, mp 84.5°-85° C.; 300 MHz $^1$H NMR (d, CDCl₃) 7.60-7.30 (m, 20H), 5.65 (s, 1H), 5.18 (AB quartet, $u_{AB}$=20.5 Hz, $J_{AB}$=11.0 Hz, 2H, Z-CH₂), 4.91 (dd, $J_{1,1'}$=11.0 Hz, $J_{1,2}$=4.4 Hz, 1H, H₆), 4.83 (Ab quartet, $u_{AB}$=28.6 Hz, $J_{AB}$=11.6 Hz, 2H, PhCH₂O), 4.64 (AB quartet, $u_{AB}$=19.0 Hz, $J_{AB}$=11.8 Hz, 2H, PhCH₂O), 4.15 (t, $J_{6,6'}$=10.6 Hz, $J_{5,6'}$=10.6 Hz, 1H, H₆'), 4.97 (dd, $J_{4,5}$=10.3 Hz, $J_{3,4}$=8.6 Hz, 1H, H₄), 3.86 (dd, $J_{1,1'}$=13.5 Hz, $J_{1,2}$=2.6 Hz, 1H, H₁), 3.77 (dd, $J_{3,4}$=8.6 Hz, $J_{2,3}$=4.7 Hz, 1H, H₃), 3.68-3.62 (m, 1H, H₂) and 3.61-3.49 (m, 2H, H₁, and H₅); 75 Hz $^{13}$C NMR (CDCl₃) 156.4, 138.9, 138.5, 138.2, 136.7, 129.5, 129.2, 129.0, 128.9, 128.8, 128.6, 128.5, 128.3, 128.2, 126.6, 101.8, 82.5, 81.3, 77.9, 74.5, 72.1, 70.5, 68.1, 53.0 and 45.4 ppm; and mass spectrum (m/e) 572 (M+Li).

EXAMPLE 3

Preparation of N-carbobenzoxy-2,3-di-O-benzyl-1-deoxynojirimycin

To a solution of 27.2 g (0.048 mol) of N-carbobenzoxy-2,3-di-O-benzyl-4,6-O-benzylidene-1-deoxynojirimycin in 250 mL of dichloromethane was added 200 mL of 50% aqueous trifluoroacetic acid. The biphasic mixture was stirred vigorously for 3 hours, and an additional 200 mL of 50% aqueous trifluoroacetic acid was added and stirring continued for an additional two hours. The layers were separated, the organic layer washed with saturated aqueous sodium bicarbonate, dried and concentrated. The crude material was chromatographed to remove benzaldehyde with 50:50 methylene chloride/hexane as eluant and recrystallized from methylene chloride/hexane to afford 15.5 g (68% yield) of N-carbobenzoxy-2,3-di-O-benzyl-1-deoxynojirimycin as a white solid, mp 115°-116° C.; $^1$H NMR (d, d₆-acetone); 7.40-7.20 (m, 15H), 5.15 (brs, 2H, ZCH₂), 4.70 (AB quartet, $u_{AB}$@25 Hz, $J_{AB}$=12 Hz, 2H, OCH₂Ph), 4.65 (AB quartet, $u_{AB}$=60 Hz, $J_{AB}$=12 Hz, 2H, OCH₂Ph) 4.36 (br d, 1H), 4.25 (br s, 1H), 4.04-3.88 (m, 1H), 3.78-3.91 (m, 3H), 3.70 (br t, J=Hz, 1H) and 3.33 (br d, J=Hz, 1H, H₁'); 75 MHz $^{13}$C NMR (CDCl₃) 157.6, 137.7, 137.4, 137.0, 129.2, 129.1, 128.7, 128.6, 128.3, 128.2, 75.7, 74.3, 73.3, 71.6, 68.1, 67.9, 61.9 and 60.8 ppm; and mass spectrum (m/e) 484 (M+Li). Note: Both $^1$H and $^{13}$C spectrum display rotomers which make assignments difficult.

EXAMPLE 4

Preparation of N,6-O-Carbamoyl-2,3-di-O-benzyl-1-deoxynojirimycin

To a mixture of 15.5 g (32.6 mmol) of N-carbobenzoxy-2,3-di-O-benzyl-1-deoxynojirimycin and 8.12 g (32.6 mmol) of di-n-butyltin-oxide was added 400 mL of toluene and the solution was refluxed for 3 hours with azeotropic removal of water.

The reaction was cooled to room temperature and concentrated in vacuo. The residue was diluted with ethyl acetate and the majority of tin salts were removed by filtration. The filtrate was washed with saturated sodium bicarbonate, dried over magnesium sulfate, filtered, and concentrated in vacuo. The residue was recrystallized from dichloromethane and hexane to afford 9.2 g (78% yield) of N,6-O-carbamoyl-2,3-di-O-benzyl-1-deoxynojirimycin, mp 118°-119° C.; 300 MHz $^1$H NMR (d, CD₃OD) 7.50-7.20 (m, 10H), 4.86 (br s, 2H, PhCH₂O) 4.70 (AB quartet, $u_{AB}$=18.5 Hz, $J_{AB}$=11.7 Hz, 2H, OCH₂Ph), 4.47 (t, $J_{6,6'}$=8.3 Hz, $J_{5,6}$=8.3 Hz, 1H, H₆'), 4.26 (dd, $J_{6,6'}$=8.3 Hz, $J_{5,6}$=4.2 Hz, 1H, H₆), 4.06 (dd, $J_{1,1'}$=12.7 Hz, $J_{1,2}$=5.4 Hz, 1H, H₁), 3.62 (ddd, $J_{5,6'}$=8.3 Hz, $J_{5,6}$=4.2 Hz, $J_{4,5}$=9.2 Hz, 1H, H₅), 3.55-3.40 (complex m, 3H, H₂, H₃ and H₄) and 2.83 (dd, $J_{1,1'}$=12.7 Hz, $J_{1',2}$=10.0 Hz, 1H, H₁'); 75 MHz $^{13}$C NMR (CDCl₃) 157.4, 138.8, 138.1, 129.2, 129.1, 128.6, 128.5, 128.3, 85.0, 77.8, 76.0, 73.4, 73.2, 66.2, 57.5 and 43.6 ppm; and mass spectrum (m/e) 370 (M+H).

EXAMPLE 5

Preparation of N,6-O-Carbamoyl-2,3-di-O-benzyl-1,5-dideoxy-1,5-imino-D-galactitol To a solution of 2.60 mL (36.7 mmol, 1.5 eq) of dry dimethyl sulfoxide in 100 mL of dry dichloromethane at −60° C. under a nitrogen atmosphere was added, with overhead stirring, 4.5 mL (3.18 mol, 1.3 eq) of trifluoroacetic anhydride dropwise over twenty minutes. The reaction was stirred for an additional ten minutes. To this was added dropwise a solution of 9.0 g (24.5 mmol) of N,6-O-carbamoyl-2,3-di-O-benzyl-1-deoxynojirimycin in 100 mL of methylene chloride over 30 minutes. The reaction was stirred an additional 45 minutes at −60° C. The ice bath was removed and the reaction was quenched with 7.0 g (69.1 mmol) of triethylamine. The reaction was warmed to room temperature, washed with 200 mL of 1N aqueous hydrochloric acid, 100 mL saturated sodium bicarbonate, 100 mL of brine and concentrated in vacuo, azeotroped 2×100 mL with toluene to yield 9.0 grams of crude ketone. This was dissolved in 400 mL of tetrahydrofuran and 10 mL of methanol. The solution was cooled to −15° C. and 0.900 g (23.7 mmol) of sodium borohydride was added carefully with stirring over ten minutes, followed by quenching with 200 mL of saturated ammonium chloride solution. The solution was diluted with 200 mL of ethyl acetate and the organic layer was separated, washed with water and dried over magnesium sulfate, filtered and concentrated in vacuo to yield 8.80 grams of a mixture of glucitol and galactitol isomers in a ratio of 20:80, respectively. The crude material was recrystallized from hot ethyl acetate to afford 4.50 g (50% yield) of N,6-O-carbamoyl-2,3-O-benzyl-1,5-dideoxy-1,5-imino-D-galactitol as a white solid, mp 157°-158° C.; 400 MHz, $^1$H NMR (de CDCl₃) 7.38-7.26 (m, 10H), 4.76 (AB quartet, $u_{AB}$=33.7 Hz, $J_{AB}$=11.67 Hz, 2H, OCH₂Ph) 4.70 (AB quat, $u_{AB}$=14.3 Hz, $J_{AB}$=11.4 Hz, 2H, OCH₂Ph) 4.43 (dd, $J_{6,6'}$=8.6 Hz, $J_{5,6}$=4.6 Hz, 1H, H₆), 4.29 (t, $J_{6,6'}$=8.6 Hz, $J_{5,6'}$=8.6 Hz, 1H, H₆'), 4.21 (dd, $J_{1,1'}$=13.3 Hz, $J_{1,2}$=6.1 Hz, 1H, H₁), 3.92 (t, $J_{3,4}$=2.6 Hz, $J_{4,5}$=2.0 Hz, 1H, H₄), 3.87 (ddd, $J_{1',2}$=10.5 Hz, $J_{1,2}$=6.1 Hz, $J_{2,3}$=9.1 Hz, 1H, H₂), 3.73 (ddd, $J_{5,6'}$=8.6 Hz, $J_{5,6}$=4.6 Hz, $J_{4,5}$=2.0 Hz, 1H, H₅), 3.49 (dd, $J_{3,4}$=2.6 Hz, $J_{2,3}$=9.1 Hz, 1H, H₃) and 2.73 (dd, $J_{1,1'}$=13.3 Hz, $J_{1',2}$=10.5 Hz, 1H, H₁'); 75 MHz $^{13}$C NMR (CDCl₃) 157.3, 138.0, 137.7, 128.7, 128.6, 128.2, 128.1, 127.9, 127.8, 81.5, 73.4, 73.3, 73.1, 67.6, 62.6, 55.8 and 43.1 ppm; and mass spectrum (m/e) 370 (M+H).

EXAMPLE 6

Preparation of N,6-O-Carbamoyl-2,3-di-O-benzyl-1,4-dideoxy-4-fluoronojirimycin To a solution of 6.00 g (16.3 mmol) of N,6-O-carbamoyl-2,3-di-O-benzyl-1,5-dideoxy-1,5-imino-D-galactitol in 75 mL of anhydrous dichloromethane at −78° C. under a nitrogen atmosphere was added 3.87 mL (47.8 mmol, 3 eq) of anhydrous pyridine and then 6.48 mL (7.90 g, 49 mmol) of diethylaminosulfur trifluoride. The solution was warmed to room temperature and then refluxed for six hours. The reaction was cooled to room temperature and poured into 300 mL saturated aqueous sodium bicarbonate at 0° C. The solution was extracted 2×50 mL with dichloromethane. The combined extracts were washed with 1N aqueous hydrochloric acid, saturated aqueous sodium bicarbonate, and brine, dried over magnesium sulfate, filtered and concentrated to yield 5.5 g of crude product. Purification by silica gel column chromatography using dichloromethane as eluant afforded 4.6 grams (66% yield) of pure material which was identified as N,6-O-carbamoyl-2,3-di-O-benzyl-1,4-dideoxy-4-fluoronojirimycin, mp 143°–144° C.; $^1$H NMR (d, CDCl$_3$) 7.39–7.26 (m, 10H), 4.84 (br s, 2H, PhCH$_2$O), 4.71 (AB quartet, u$_{AB}$=15.9 Hz, J$_{AB}$=11.4 Hz, 2H, OCH$_2$Ph), 4.45 (dd, J$_{6,6'}$=9.2 Hz, J$_{5,6'}$=7.8 Hz, 1H, H$_6$), 4.31 (dt, J$_{4,F}$=51.2 Hz, J$_{3,4}$=8.9 Hz, J$_{4,5}$=8.9 Hz, 1H, H$_4$), 4.27 (dd, J$_{6,6'}$=9.2 Hz, J$_{5,6}$=4.0 Hz, 1H, H$_6$), 4.13 (ddd, J$_{1,1'}$=13.3 Hz, J$_{1,2}$=5.9 Hz, J$_{1,F}$=1.6 Hz, 1H, H$_1$), 3.73 (dddd, J$_{4,5}$=8.9 Hz, J$_{5,6}$=4.0 Hz, J$_{5,6'}$=7.8 Hz, J$_{5,F}$=6.5 Hz, 1H, H$_5$), 3.64 (dt, J$_{3,4}$=8.9 Hz, J$_{2,3}$=8.9 Hz, J$_{3,F}$=12.3 Hz, 1H, H$_3$), 3.53 (ddd, J$_{1,2}$=5.8 Hz, J$_{1',2}$=10.0 Hz, J$_{2,3}$=8.9 Hz, 1H, H$_2$), 2.80 (dd, J$_{1,1'}$=13.3 Hz, J$_{1',2}$=10.0 Hz, 1H, H$_{1'}$); 75 MHz $^{13}$C NMR (CDCl$_3$) 157.3, 138.8, 138.4, 129.4, 129.2, 128.8, 128.7, 128.6, 128.5, 93.1 (d, J$_{C4,F}$=187.1 Hz, C$_4$), 83.2 (d, J$_{C3,F}$=15.9 Hz, C$_3$), 76.2 (d, J$_{C2,F}$=8.6 Hz, C$_2$), 75.9, 74.1, 65.6, 55.4 (d, J$_{C5,F}$=28.5, Hz, C$_5$) and 43.2 ppm; and mass spectrum (m/e) 372 (M+H).

EXAMPLE 7

Preparation of 2,3-Di-O-benzyl-1,4-dideoxy-4-fluoronojirimycin

To a solution of 4.1 g (11.1 mmol) of N,6-O-carbamoyl-2,3-di-O-benzyl-1,4-dideoxy-4fluoronojirimycin in 400 mL of a 50:50 mixture of tetrahydrofuran and methanol was added 25 mL of 10% aqueous potassium hydroxide and the solution refluxed for three hours. The solution was cooled to room temperature, concentrated, partitioned with water and dichloromethane and then extracted 2×50 mL with dichloromethane. The combined organics were dried over magnesium sulfate, filtered and concentrated to yield 3.75 g of crude product which was purified by silica gel chromatography using 5% methanol, 95% methylene chloride as eluant. In this manner one obtains 3.32g (924 yield) of 2,3-di-O-benzyl-1,4-dideoxy-4-fluoronojirimycin; 400 MHz $^1$H NMR (d, CDCl$_3$) 7.48–7.28 (m, 10H), 4.85 (AB quartet, u$_{AB}$=19.4 Hz, J$_{AB}$=11.0 Hz, 2H, OCH$_2$Ph), 4.70 (AB quartet, u$_{AB}$=33.9, J$_{AB}$=11.5 Hz, 2H, OCH$_2$Ph), 4.30 (dt, J$_{4,F}$=50.7 Hz, J$_{4,5}$=9.0 Hz, J$_{3,4}$=9.0 Hz, 1H, H$_4$), 3.85 (ddd, J$_{6,6'}$=10.8 Hz, J$_{5,6}$=2.9 Hz, J$_{6,F}$=1.8 Hz, 1H, H$_6$), 3.66 (dd, J$_{6,6'}$=10.8 Hz, J$_{5,6'}$=5.7 Hz, 1H, H$_{6'}$), 3.61 (dt, J$_{3,F}$=14.8 Hz, J$_{2,3}$=J$_{3,4}$=9.0 Hz, 1H, H$_3$), 3.45 (ddd, J=10.8 Hz, J=10.8 Hz, J=5.8 Hz, 1H), 3.23 (ddd, J=12.7, J=5.2, J=1.8, 1H), 2.75 (dddd, J$_{4,5}$=9.0 Hz, J$_{5,6'}$=5.7 Hz, J$_{5,6}$=2.9 Hz, J$_{5,F}$=12.8 Hz, 1H, H$_5$) and 2.53 (dd, J$_{1,1'}$=12.3 Hz, J$_{1',2}$=10.7 Hz, 1H, H$_{1'}$); and 101 MHz $^{13}$C-NMR (CDCl$_3$) 138.7, 138.4, 28.4, 128.3, 127.9, 127.8, 127.7, 92.4 (d, J$_{C4,F}$=182.6 Hz, C$_4$), 84.6 (d, J$_{3,F}$=16.5 Hz, C$_3$), 79.3 (d, J$_{2,F}$=8.5 Hz, C$_2$), 75.1, 73.2, 62.2, 59.8 (d, J$_{5,F}$=21.3 Hz, C$_5$) and 48.1 ppm.

EXAMPLE 8

Preparation of 1,4-Dideoxy-4-fluoronojirimycin

To a solution of 3.32 g (10.2 mmol) of 2,3-di-O-benzyl-1,4-dideoxy-4-fluoronojirimycin in 50 mL of glacial acetic acid and 10 mL of methanol was added 3.0 grams of 10% palladium on carbon. The solution was purged with nitrogen, then charged with 50 psig hydrogen and stirred for 48 hrs at room temperature. The catalyst was removed by filtration and the solution was concentrated in vacuo. The oil was taken up in 10 mL of water and lyophilized to yield 2.3 grams of the acetate salt which was converted to the free base by passage over a 10 mL column of CG 400 (hydroxide form) resin. The eluant was lyophilized to yield 1.44 g (85% yield) of the desired 1,4-dideoxy-4-fluoronojirimycin as a clear foam; 400 MHz $^1$H NMR (d, D$_2$O) 4.18 (dt, J$_{4,F}$=50.7 Hz, J$_{3,4}$=9.1 Hz, J$_{4,5}$=9.1 Hz, 1H, H$_4$) 3.76 (dt, br dt, J$_{6,6'}$=12.1 Hz, J$_{5,6}$=3.0, 1H, H$_6$), 3.69 (dd, J$_{6,6'}$=12.1 Hz, J$_{5,6'}$=5.1 Hz, 1H, H$_{6'}$), 3.61 (dt, J$_{3,F}$=14.7 Hz, J$_{3,4}$=9.1 Hz, J$_{2,3}$=9.1 Hz, 1H, H$_3$), 3.51 (ddd, J$_{2,3}$=9.1 Hz, J$_{1,2}$=5.2 Hz, J$_{1',2}$=10.7 Hz, 1H, H$_2$), 3.09 (ddd, J$_{1,1'}$=12.6 Hz, J$_{1,2}$=5.2 Hz, J$_{1,F}$=1.5 Hz, 1H, H$_1$), 2.70 (dddd, J$_{4,5}$=9.1 Hz, J$_{5,6'}$=5.1 Hz, J$_{5,6}$=3.0 Hz, J$_{5,F}$=4.7 Hz, 1H, H$_5$) and 2.45 (dd, J$_{1,1'}$=12.6 Hz, J$_{1',2}$=10.7 Hz, 1H, H$_{1'}$); 101 MHZ $^{13}$C NMR (D$_2$O) 94.5 (d, J$_{C4,F}$=180.1 Hz, C$_4$), 79.3 (d, J$_{C3,F}$=16.8 Hz, C$_3$) 73.7 (d, J$_{C2,F}$=8.3 Hz, C$_2$), 63.3, 61.4 (d, J$_{C5,F}$=19.8 Hz, C$_5$) and 51.3 ppm; and mass spectrum (m/e) 166 (M+H).

EXAMPLE 9

Preparation of N-Butyl-1,4-dideoxy-4-fluoronojirimycin

To a solution of 700 mg (4.2 mmol) of 1,4-dideoxy-4-fluoronojirimycin in 10 mL of methanol and 10 mL of methanol was added 250 mg of 10% palladium on carbon. The reaction was charged with 820 mL (670 mg, 9.3 mmol) of n-butanal and purged with nitrogen, then placed under 20 psi of hydrogen for 24 hours. An additional 820 ml of n-butanal was added and the reaction stirred for 48 hours. The solution was purged with nitrogen and filtered through celite to remove catalyst. The filtrate was concentrated to yield 790 mg of crude product which was purified by column chromatography over silica gel using 15% ethanol/85% methylene chloride as eluant to afford 670 mg of the desired compound. This was crystallized from ethanol/hexane to yield 330 mg (36% yield) of high purified material which was identified as N-butyl-1,4-dideoxy-4-fluoronojirimycin, mp 127.6–128.6; 400 MHz $^1$H NMR (d, CD$_3$OD) 4.25 (dt, J$_{4,F}$=50.2 Hz, J$_{3,4}$=8.6 Hz, J$_{4,5}$=9.3 Hz, 1H, H$_4$), 3.87 (dt, J$_{6,6'}$=12. 2 Hz, J$_{5,6}$=2.4 Hz, J$_{6,F}$=2.4 Hz, 1H, H$_6$), 3.72 (dt, J$_{6,6'}$=12.2 Hz, J$_{5,6'}$=2.4 Hz, J$_{6',F}$=2.4 Hz, 1H, H$_{6'}$), 3.46 (ddd, J$_{1,2}$=5.0 Hz, J$_{1',2}$=10.1 Hz, J$_{2,3}$=8.9 Hz, 1H, H$_2$), 3.36 (dt, J$_{3,F}$=15.9 Hz, J$_{2,3}$=8.9 Hz, J$_{3,4}$=8.6 Hz, 1H, H$_3$), 2.98 (dd, J$_{1,1'}$=11.5 Hz, J$_{1,2}$=5.0 Hz, 1H, H$_1$), 2.80 (dt, J=13.3 Hz, J=7.5 Hz, 1H, NCH$_A$), 2.57 (ddd, J=13.3 Hz, J=7.7 Hz, J=8.5, 1H, NCH$_B$), 2.28 (dddd, J$_{4,5}$=9.4

Hz, $J_{5,6'}=2.3$ Hz, $J_{5,6}=2.3$ Hz, $J_{5,F}=5.6$ Hz, 1H, $H_5$), 2.16 (t, $J_{1,1'}=11.0$ Hz, $J_{1',2}=10.1$ Hz, 1H, $H_{1'}$), 1.46 (m, 2H), 1.31 (m, 2H), and 0.94 (t, 3H); 101 MHz $^{13}$C NMR (CD$_3$OD) 93.6 (d, $J_{C4,F}=179.8$ Hz, $C_4$), 79.4 (d, $J_{C4,F}=19.9$ Hz, $C_4$), 71.4 (d, $J_{C2,F}=11.4$ Hz, $C_2$), 66.0 (d, $J_{C5,F}=19.9$ Hz, $C_5$), 59.6, 58.0, 54.3, 28.1, 23.0 and 16.2 ppm; mass spectrum (m/e) 222 (M+H) and 204; and Anal. Calcd. for $C_{10}H_{20}FNO_3$: C (54.27), H (9.13) and N (6.32); Found C (54.16), H (9.12) and N (6.31).

EXAMPLE 10

This example illustrates glycosidase inhibition activity for 1,4 dideoxy-4-fluoronojirimycin (1), and N-butyl-1,4-dideoxy-4-fluoronojirimycin (2). It is contemplated that other N-derivatives will also manifest glycosidase inhibition activity.

The glycosidase inhibition activity is determined by modifying an assay procedure described in Evans et al, Phytochemistry, 22, pp. 768-770 (1983). More particularly, yeast α-glucosidase and almond β-glucosidase activities were measured by the Evans et al method which was modified by assaying activities at pH 7.4 in N-2-hydroxyethylpiperazine-N-2-ethane sulfonic acid (HEPES) buffer, measuring in 96 well microtiter plates, and including 10% DMSO in control and test samples.

The release of p-nitrophenol from the substrate p-nitrophenylglycoside was measured spectrophotometrically in the presence and absence of test compound. Each assay included a known inhibitor of the enzyme as a standard. IC$_{50}$ values were determined for compounds which inhibited the enzymes more than 50% at a 1 millimolar concentration.

α-Glucosidase Inhibition Assay

PH 7.4

To 100 ul 50 mM HEPES buffer, pH 7.4, in a microtiter plate, 20 ul test compound in DMSO (DMSO alone in control)and 40 ul (0.013 units) yeast α-glucosidase (Sigma) in HEPES buffer were added and preincubated at room temperature 15 minutes. 40 ul 1.25 mM p-nitrophenyl-α-D-glucopyranoside (Sicjma) in HEPES buffer, as substrate was added and the absorbance change at 405 nm was monitored in a Biotek EIA Autoreader. Absorption change was measured at 15 to 25 minutes (reaction was linear for at least 30 minutes). Each sample was tested in triplicate. IC$_{50}$ values were determined from the linear portion of the log concentration vs percent inhibition curve obtained from a minimum of 3 points. Deoxynojirimycin was used as standard inhibitor.

β-Glucosidase Inhibition Assay pH 7.4:

To 100 ul 50 mM HEPES buffer, pH 7.4, in a microtiter plate, 20 ul test compound in DMSO (DMSO alone in control) and 40 ul (.136 units) β-glucosidase (Sigma) in HEPES buffer were added and preincubated at room temperature 15 minutes. 40 ul 1.25 mM p-nitrophenyl-β-D-glucopyranoside in HEPES buffer was added as substrate and the absorbance change at 405 nm was monitored utilizing a Biotek EIA Autoreader. Absorption change was measured at 15 to 25 minutes (reaction is linear for at least 30 minutes). Each sample was tested in triplicate. IC$_{50}$ values were determined from the linear portion of the log concentration vs percent inhibition curve obtained from a minimum of 3 points. Castanospermine was used as standard inhibitor.

pH 4.8:

To 100 ul 50 mM sodium citrate buffer, pH 4.8, in a microtiter plate, 20 ul test compound in DMSO (DMSO alone in control) and 20 ul (.017 units) β-glucosidase (Sigma) in citrate buffer were added and preincubated at room temperature 15 minutes. 20 ul 2.50 mM p-nitrophenyl-β-D-glucopyranside in citrate buffer was added as substrate and incubated at room temperature 20 minutes (reaction is linear for at least 30 minutes). 50 ul 0.4M NaOH was added and the absorption change at 405 nm was determined utilizing a Biotek EIA Autoreader. Each sample was tested in triplicate. IC$_{50}$ values were determined from the linear portion of the log concentration vs percent inhibition curve obtained from a minimum of 3 points. Castanospermine was used as standard inhibitor.

TABLE 1

| | Enzyme Inhibition Data | | | | |
|---|---|---|---|---|---|
| COMPOUND NO. | ALPHA GLUCO SIDASE pH 7.4 | BETA GLUCO SIDASE- pH 4.8 | BETA GLUCO SIDASE- pH 7.4 | ALPHA MANNO SIDASE- pH 4.5 | ALPHA MANNO SIDASE- pH 7.4 |
| 1 | 18% 5 mM | 17% 5 mM | 13% 5 mM | −2% 5 mM | 12% 5 mM |
| 2 | 28% 5 mM | 13% 5 mM | 14% 5 mM | −3% 5 mM | 6% 5 Mm |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound represented by the formula:

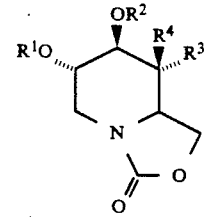

wherein $R^1$ and $R^2$ represent hydroxy protecting groups; $R^3$ represents hydrogen, hydroxy and fluorine; and $R^4$ represents hydrogen and hydroxy wherein when $R^4$ is hydroxy, $R^3$ is hydrogen, and when $R^4$ is hydrogen, $R^3$ is hydroxy or fluorine; or $R^3$ and $R^4$ together represent keto.

2. A compound of claim 1 wherein $R^3$ is hydroxy and $R^4$ is hydrogen.

3. A compound of claim 1 wherein $R^3$ is F and $R^4$ is hydrogen.

4. A compound of claim 1 wherein $R^4$ is hydroxy and $R^3$ is hydrogen.

5. A compound of claim 1 wherein $R^3$ and $R^4$ together represent keto.

6. Glycosidase inhibiting composition comprising a compound of claim 1 and a pharmaceutically acceptable diluent and/or carrier.

7. Method of making a compound of claim 3 comprising:

a) protecting the 4-hydroxy and 6-hydroxy groups of an N-carbobenzoxy-1-deoxynojirimycin compound;

b) reacting the resulting N-carbobenzoxy-4,6-O-protected-1-deoxynojirimycin with a hydroxy protecting agent;

c) reacting the resulting product of b) with an agent to deprotect the 4-hydroxy and 6-hydroxy groups;

d) reacting the reaction product of c) under conditions which cause the carbo-part of the carbobenzoxy group and the 6-hydroxy group to cyclize with concomitant removal of the benzoxy moiety;

e) inverting the 4-hydroxy group; and f) reacting the product of e) with a fluorine source.

* * * * *